United States Patent [19]

Briggs et al.

[11] 4,193,919

[45] Mar. 18, 1980

[54] PROCESS FOR PREPARING RIFAMYCIN S USING A STRONG ACID CATION EXCHANGE RESIN

[75] Inventors: Roger A. Briggs; Jo Ann Gilpin, both of Midland, Mich.

[73] Assignee: The Dow Chemical Company, Midland, Mich.

[21] Appl. No.: 29,233

[22] Filed: Apr. 11, 1979

[51] Int. Cl.$^2$ .................. C07D 491/18; C07D 491/08
[52] U.S. Cl. ............................................. 260/239.3 P
[58] Field of Search .................................. 260/239.3 P

[56] References Cited

FOREIGN PATENT DOCUMENTS 924472  4/1963  United Kingdom .............. 260/239.3 P Primary Examiner—Alan L. Rotman
Assistant Examiner—Robert T. Bond

[57] ABSTRACT

A process for converting rifamycin O to rifamycin S using a strong acid cation exchange resin to catalyze the reaction and a solvent containing up to about 13% water to dissolve the rifamycin derivatives.

4 Claims, No Drawings

PROCESS FOR PREPARING RIFAMYCIN S USING A STRONG ACID CATION EXCHANGE RESIN

BACKGROUND OF THE INVENTION

The antibiotic rifamycin S is a derivative of the fermentation product rifamycin B. Rifamycin B is first oxidized to the intermediate compound rifamycin O. Rifamycin O then may be hydrolyzed to give Rifamycin S. This second step is generally carried out using aqueous sulfuric acid as a catalyst. This procedure for converting rifamycin O to rifamycin S is not satisfactory for a continuous process. Therefore, an improved process for carrying out this conversion is commercially desirable. The structure of rifamycin O and rifamycin S may be represented as follows:

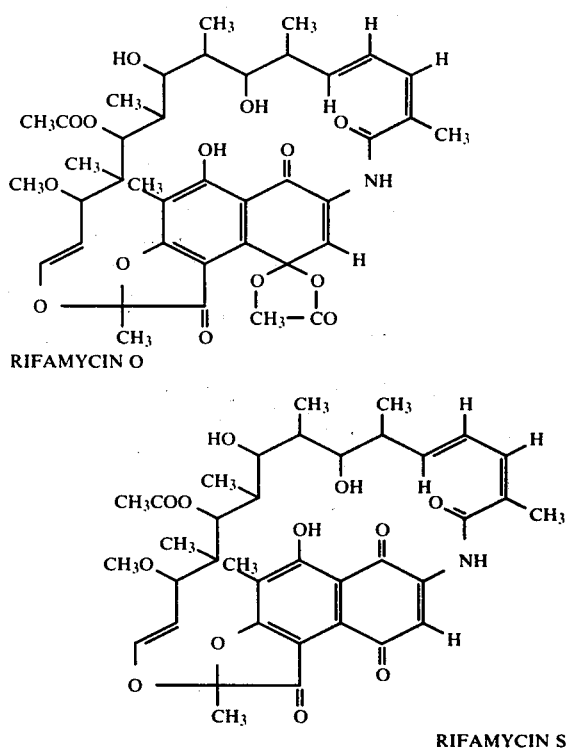

RIFAMYCIN O

RIFAMYCIN S

SUMMARY OF THE INVENTION

The present invention is directed toward a high yield process for converting rifamycin O to rifamycin S which comprises contacting rifamycin O with a strong acid cation exchange resin in a suitable solvent or solvent mixture containing from about 0.4 percent to about 15 percent water at a temperature of from about 20° C. to about 55° C. for a time sufficient to convert a substantial amount of the rifamycin O to rifamycin S. As used herein the term suitable solvent refers to a solvent or solvent mixture in which rifamycin O and rifamycin S show satisfactory solubility and in which the hydrolysis reaction will occur without the formation of excess impurities. Suitable solvents which may be used in the present invention include, but are not limited to, tetrahydrofuran, chloroform, dioxane, methylene chloride, methanol, or the like. Generally, a solvent mixture containing an alcohol such as methanol or ethanol or a glycol such as ethylene glycol in combination with a non-polar solvent such as tetrahydrofuran, dioxane or chloroform is preferred.

Although the present invention may be carried out with any strong acid cation exchange resin in the hydrogen form, a sulfonated cation exchange resin is generally preferred. As used herein the term strong acid cation exchange resin refers to a resin capable of exchanging cations. For example, such resins will exchange sodium for calcium and magnesium or hydrogen for calcium, magnesium, and sodium as in "salt splitting". Such a resin is usually prepared by the nuclear sulfonation of a copolymer backbone, generally of styrene and divinylbenzene. Resins of this general type are well known to those skilled in the art and several ion exchange resins which may be used to carry out the process described herein are commercially available.

The present invention has the further advantage of making it possible to carry out the hydrolysis of rifamycin O in a continuous process operation.

DETAILED DESCRIPTION OF THE INVENTION

In carrying out the present invention Dowex® MSC-1 (Dow) cation exchange resin was found to be satisfactory. This resin is described as a strong acid macroporous cation exchange resin having sulfonic acid active ion exchange groups attached to a styrene-divinyl-benzene copolymer backbone. See U.S. Pat. No. 3,549,562. Dowex® 50 described as a strongly acidic cation exchange gel-type resin having nuclear sulfonation and having 10% crosslinking agent would also be suitable for use with present invention. Other comparable resins known to those skilled in the art would also be operable. In carrying out the process that is the current invention, the solution containing rifamycin O is contacted with the strong acid cation resin as described above by mixing the solution and the resin together in a container as in a batch process or by running a stream of the solution through a bed of resin as for example in a continuous process.

Preferred solvents for carrying out the present process include tetrahydrofuran, dioxane, and chloroform with tetrahydrofuran being particularly preferred. Most preferably, the solvent will also contain from about 5 percent to about 30 percent methanol to reduce the formation of impurities during the hydrolysis. From about 0.4 percent to about 15 percent water must also be present during the reaction and is most conveniently added along with the solvent. From about 0.5 to 7.5 percent water was found to give the best results. Although water is an essential reactant in the hydrolysis of rifamycin O to rifamycin S, excess water slows the reaction.

The reaction is preferably carried out at slightly above room temperature. Higher temperatures were found to increase the rate of the reaction, but also increased the rate of degradation of rifamycin S resulting in greater impurities in the final product. Lower temperatures, although slowing the reaction, minimized the presence of degradation products. The process that is the subject of the present invention when practiced as herein described has been found to give yields of between about 80 and 90 percent.

One skilled in the art will appreciate that it is not possible to give optimal process conditions for all the variations of the invention herein described. The exact conditions required to give optimal performance will vary with the specific strong acid ion exchange resin used, the concentration of rifamycin O, the solvent or solvent mixture used, and whether the process is carried out as a batch or as a continuous process. In general, operation at higher temperatures or at lower water concentrations or at a high resin ratio will give a faster rate of hydrolysis and a faster rate of degradation of rifamycin S to undesirable by-products. Decreasing the amount of methanol also was found to increase the rate of degradation. Operation of the process at lower temperatures, higher water concentration, or lower resin ratios was found to give slower hydrolysis, slower degradation of product, and ultimately higher selectivity for rifamycin S. Increasing the percent of methanol also resulted in higher selectivity.

The following example will serve to further illustrate the present invention, but is not to be construed as a limitation thereon.

EXAMPLE 1

Preparation of Resin: The resin (Dowex® MSC-1 cation exchange resin by The Dow Chemical Company) in the hydrogen form was converted to the sodium form with excess sodium hydroxide and reconverted to the hydrogen form with excess sulfuric acid. The resin was washed with water at about 25° C., washed a second time at 80°–85° C. and finally washed with and stored under methanol. The resin beads were vacuum dried (60° C./28 mmHg) overnight just before use.

Hydrolysis of Rifamycin O: The dried resin (2.0 grams) was placed in the reaction vessel. The solvent mixture (10 ml) comprising 2.5% water, 30% methanol and the balance tetrahydrofuran and also containing 1% by weight of rifamycin O was added to the resin. The reaction vessel was closed, held at 25° C., and shaken. At various intervals, samples were removed and analyzed for rifamycin S by high performance liquid chromatography. The results obtained at various time intervals are shown in the table below.

TABLE

| Reaction Time (Hrs.) | % of Theoretical Rifamycin S | % of Original Rifamycin O | Approx. % Degradation Product |
|---|---|---|---|
| 1 | 2.5 | 97 | — |
| 4 | 12 | 88 | — |
| 9 | 33 | 67 | — |
| 23 | 61 | 36 | 3.2 |
| 48 | 81 | 9 | 10 |

These data illustrate that the rifamycin O was hydrolyzed to rifamycin S using the method described herein to give a yield in excess of 80 percent if allowed to run for a period of 48 hours under the conditions of the demonstration.

We claim:

1. A process for converting rifamycin O to rifamycin S which comprises contacting the rifamycin O with a strong acid cation exchange resin in a suitable solvent or solvent mixture containing from about 0.4 percent to about 15 percent water at a temperature of from about 20° C. to about 55° C. for a time sufficient to convert a substantial amount of the rifamycin O to rifamycin S and recovering the rifamycin S.

2. The process of claim 1 wherein the cation exchange resin contains sulfonic acid active groups and the solvent mixture contains an alcohol or a glycol.

3. The process of claim 2 wherein the solvent mixture contains from about 5 percent to about 30 percent methanol and the balance of the solvent mixture is selected from the group consisting essentially of tetrahydrofuran, dioxane, methylene chloride, and chloroform.

4. The process of claim 3 wherein the solvent mixture contains from about 0.5 percent to about 7.5 percent water.

* * * * *